(12) United States Patent
    Cedarbaum et al.

(10) Patent No.: US 10,272,082 B2
(45) Date of Patent: Apr. 30, 2019

(54) COMBINATION ALS THERAPY

(75) Inventors: Jesse Cedarbaum, San Francisco, CA (US); John Mao, Millbrae, CA (US); Fady Malik, Burlingame, CA (US); Andrew A. Wolff, San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 14/131,649

(22) PCT Filed: Jul. 12, 2012

(86) PCT No.: PCT/US2012/046523
§ 371 (c)(1),
(2), (4) Date: May 5, 2014

(87) PCT Pub. No.: WO2013/010015
PCT Pub. Date: Jan. 17, 2013

(65) Prior Publication Data
US 2014/0243344 A1    Aug. 28, 2014

Related U.S. Application Data

(60) Provisional application No. 61/507,381, filed on Jul. 13, 2011, provisional application No. 61/544,533, filed on Oct. 7, 2011, provisional application No. 61/637,759, filed on Apr. 24, 2012, provisional application No. 61/637,770, filed on Apr. 24, 2012, provisional application No. 61/646,699, filed on May 14, 2012.

(51) Int. Cl.
*A61K 31/428*    (2006.01)
*A61K 31/4985*    (2006.01)

(52) U.S. Cl.
CPC ........ *A61K 31/4985* (2013.01); *A61K 31/428* (2013.01)

(58) Field of Classification Search
USPC ........................................................ 514/249
See application file for complete search history.

(56) References Cited

U.S. PATENT DOCUMENTS

| | | |
|---|---|---|
| 3,507,866 A | 4/1970 | Jones et al. |
| 4,195,088 A | 3/1980 | Barzaghi et al. |
| 4,943,573 A | 7/1990 | Meanwell |
| 5,354,759 A | 10/1994 | Oku et al. |
| 6,162,804 A | 12/2000 | Bilodeau et al. |
| 6,232,320 B1 | 5/2001 | Stewart et al. |
| 6,579,882 B2 | 6/2003 | Stewart et al. |
| 6,638,933 B2 | 10/2003 | Gerlach et al. |
| 6,657,064 B2 | 12/2003 | Gerlach et al. |
| 7,279,580 B2 | 10/2007 | Goodacre et al. |
| 7,348,339 B2 | 3/2008 | Bailey et al. |
| 7,598,248 B2 | 10/2009 | Muci |
| 7,851,484 B2 | 12/2010 | Morgan et al. |
| 7,956,056 B2 | 6/2011 | Muci et al. |
| 7,989,469 B2 | 8/2011 | Yang et al. |
| 7,998,976 B2 | 8/2011 | Bergnes et al. |
| 8,227,603 B2 | 7/2012 | Russell |
| 8,293,761 B2 | 10/2012 | Muci et al. |
| 8,299,248 B2 | 10/2012 | Hinken et al. |
| 8,716,291 B2 | 5/2014 | Hinken et al. |
| 2003/0083318 A1 | 5/2003 | Julien |
| 2003/0220365 A1 | 11/2003 | Stewart et al. |
| 2004/0023972 A1 | 2/2004 | Sundermann et al. |
| 2004/0166137 A1 | 8/2004 | Lackey |
| 2004/0235801 A1 | 11/2004 | Julien |
| 2005/0197328 A1 | 9/2005 | Bailey et al. |
| 2005/0250794 A1 | 11/2005 | Napper et al. |
| 2006/0019952 A1 | 1/2006 | Distefano et al. |
| 2006/0148805 A1 | 7/2006 | Chen et al. |
| 2007/0197507 A1 | 8/2007 | Morgan et al. |

(Continued)

FOREIGN PATENT DOCUMENTS

| | | |
|---|---|---|
| DE | 22 41 575 | 3/1973 |
| GB | 2 174 987 A | 11/1986 |

(Continued)

OTHER PUBLICATIONS

Lacomblez (Dose-ranging study of riluzole in amyotrophic lateral sclerosis, Lancet, 1996, vol. 347, pp. 1425-1431).*
ALS Association (http://www.alsa.org/news/archive/ck2017357-begins-enroll.html, Jun. 22, 2011, p. 1-3).*
Almirante. Derivatives of Imidazole. I. Synthesis and reactions of Imidazo[1,2-a]pyridines with analgesic, antiinflammatory, antipyretic and anticonvulsant activity. J. Med. Chem. 1965, 8, 305-312.
Barlin Aust. J. Chem., 25.2299-2306 (1982).
Bianchi et al., Compounds with Antiulcer and antisecretory activity. III. N-substituted imidazolones condensed with nitrogen-containing heteroaromatic rings, European Journal of Medical Chemistry (1983), 18(6), 501-6.
Bjoerk et al., Synthesis of Novel 2-Aminoimidazo [4,5-b] Pyridines, Including the Thieno Analogue of the Cooked-Food Mutagen IFP, Journal of Heterocyclic Chemistry, 43(1): 101-109 (2006).

(Continued)

*Primary Examiner* — Kathrien A Cruz
(74) *Attorney, Agent, or Firm* — Morrison & Foerster LLP

(57) ABSTRACT

Provided is a method for treating ALS in a subject, comprising administering to the subject a therapeutically effective amount of riluzole and a therapeutically effective amount of CK-2017357. Also provided are methods of reducing the variability of riluzole exposure (e.g., $C_{max}$ and/or $AUC_{24h}$) in a subject, methods of reducing the variability of riluzole exposure (e.g., $C_{max}$ and/or $AUC_{24h}$) between two or more subjects, methods of decreasing the total daily dose of riluzole in a subject, methods of increasing the half-life of riluzole in a subject, methods for decreasing the frequency of riluzole dosing in the subject, and methods for reducing the incidence and/or severity of adverse events in a subject treated with riluzole.

17 Claims, 4 Drawing Sheets

(56) References Cited

U.S. PATENT DOCUMENTS

| | | |
|---|---|---|
| 2007/0275984 A1 | 11/2007 | Imogai et al. |
| 2008/0096903 A1 | 4/2008 | Chen et al. |
| 2008/0146561 A1 | 6/2008 | Muci et al. |
| 2008/0242695 A1 | 10/2008 | Morgan et al. |
| 2009/0023724 A1 | 1/2009 | Mortensen et al. |
| 2009/0029345 A1 | 1/2009 | Russell |
| 2009/0082370 A1 | 3/2009 | Thompson et al. |
| 2009/0247538 A1 | 10/2009 | Berdini et al. |
| 2009/0247571 A1 | 10/2009 | Muci et al. |
| 2010/0022564 A1 | 1/2010 | Davies et al. |
| 2010/0173930 A1 | 7/2010 | Muci et al. |
| 2011/0014212 A1 | 1/2011 | Hinken |
| 2011/0268729 A1 | 11/2011 | Abila |
| 2011/0312975 A1 | 12/2011 | Yang et al. |
| 2014/0303366 A1 | 10/2014 | Hinken et al. |
| 2015/0065525 A1 | 3/2015 | Jasper et al. |
| 2015/0250784 A1 | 9/2015 | Malik et al. |
| 2017/0042890 A1 | 2/2017 | Shefner et al. |
| 2017/0266192 A1 | 9/2017 | Jasper et al. |

FOREIGN PATENT DOCUMENTS

| | | |
|---|---|---|
| GB | 2 190 676 A | 11/1987 |
| GB | 2 400 101 A | 6/2004 |
| IL | 40080 A | 12/1975 |
| JP | 06-041135 A | 2/1994 |
| WO | WO 99/62908 A2 | 12/1999 |
| WO | WO 2004/092166 A2 | 10/2004 |
| WO | WO 2005/002520 A3 | 1/2005 |
| WO | WO 2005/013894 A2 | 2/2005 |
| WO | WO 2005/060711 A2 | 7/2005 |
| WO | WO 2005/072412 A2 | 8/2005 |
| WO | WO 2005/108374 A1 | 11/2005 |
| WO | WO 2006/030031 A1 | 3/2006 |
| WO | WO 2006/036883 A2 | 4/2006 |
| WO | WO 2006/046024 A1 | 5/2006 |
| WO | WO 2006/088836 A2 | 8/2006 |
| WO | WO 2007/125310 A2 | 11/2007 |
| WO | WO 2007/125321 A2 | 11/2007 |
| WO | WO 2008/016648 A2 | 2/2008 |
| WO | WO-2008/016669 A2 | 2/2008 |
| WO | WO 2008/049105 A2 | 4/2008 |
| WO | WO 2008/051493 A2 | 5/2008 |
| WO | WO 2008/075007 A1 | 6/2008 |
| WO | WO 2008/089459 A1 | 7/2008 |
| WO | WO-2008/121333 A1 | 10/2008 |
| WO | WO-2009/015844 A1 | 2/2009 |
| WO | WO-2009/099594 A1 | 8/2009 |
| WO | WO 2010/068483 A2 | 6/2010 |
| WO | WO-2010/102923 A2 | 9/2010 |
| WO | WO-2010/102923 A3 | 9/2010 |
| WO | WO-2010/148409 A1 | 12/2010 |
| WO | WO-2013/151938 A1 | 10/2013 |
| WO | WO-2013/155262 A2 | 10/2013 |
| WO | WO-2015/168064 A1 | 11/2015 |

OTHER PUBLICATIONS

Bonnet et al: "Synthesis and antibronchospastic activity of 8-alkoxy- and 8-(alkylamino)imidazo(1,2-a)pyrazines" Journal of Medicinal Chemistry, vol. 35, No. 18, Jan. 1, 1992, pp. 3353-3358.

Dorwald, Side Reactions in Organic Synthesis: A Guide to Successful Synthesis Design, Weinheim: Wiley-VCH Verlag GmbH & Co., KGaA, Preface (2005).

IUPAC ED—Alan D McNaught and Andrew Wilkinson: "Alkyl groups" [Online] Jan. 1, 1997 (Jan. 1, 1997), Compendium of Chemical Terminology: IUPAC Recommendations; [IUPAC Chemical Data Series], Blackwell Science, Oxford [U.A.], XP002585005 ISBN: 978-0-86542-684-9 Retrieved from the Internet: URL:http://www.iupac.org/goldbook/A00228.pdf.

IUPAC Ed. Alan D. McNaught and Andrew Wilkinson "cycloalkyl groups" [Online] Jan. 1, 1997 (Jan. 1, 1997), Compendium of Chemical Terminology: IUPAC Recommendations; [IUPAC Chemical Data Series], Blackwell Science, Oxford [U.A.], XP002585006 ISBN: 978-0-86542-684-9 Retrieved from the Internet: URL: http://www.iupac.org/goldbook/C01498.pdf.

Jordan, Nature Reviews, Drug Discovery 2:205-213 (Mar. 2003).

Li et al., Skeletal Muscle Respiratory Uncoupling Prevents Diet-Induced Obesity and Insulin Resistance in Mice, Nature Medicine, vol. 6(10), (2000), pp. 115-1120.

Lima et al., Current Medicinal Chemistry 12(1):23-49 (2005).

Lindstroem et al., Synthesis of the Mutagenic 2-Amino-1,6-Dimethyl-Imidazo[4,5-b]Pyridine (1,6-DMIP) and Five of Its Isomers, Heterocycles, Elsevier Science Publishers B.V. (1994), 38(3), 529-40.

Meanwell et al., 1,3 Dihydro-2H-Imidazo[4,5-b]quinolin-2-ones—Inhibitors of Blood Platelet cAMP Phosphodiesterase and Induced Aggregation Journal of Medicinal Chemistry (1991), 34(9), 2906-16.

Meanwell et al., Inhibitors of Blood Platelet cAMP Phosphodiesterase. 3. 1,3-Dihydro-2H-imidazo[4,5-b]quinolin-2-one derivates with enhanced aqueous solubility, Journal of Medicinal Chemistry, 35(14): 2688-96 (1992).

Meanwell et al., Inhibitors of Blood Platelet cAMP Phosphodiesterase. 2. Structure-activity Relationships Associated with 1,3-dihydro-2H-imidazo[4,5-b]quinolin-2-ones substituted with functionalized side chains, Journal of Medicinal Chemistry, 35(14):2672-87 (1992).

Morimoto et al., "Ca2+ binding to skeletal muscle troponic C in skeletal and cardiac myofibrils", J. biochem., 105,435-439 (1989).

Niel et al., Sexual Differentiation of the Spinal Nucleus of the Bulbocavernosus is not Medicated Solely by Adrogen Receptors in Muscle Fibers, Endocrinology, (2009), 150(7), pp. 3207-3213.

Palomo, V., et al., "The potential role of glycogen synthase kinase 3 inhibitors as amyotrophic lateral sclerosis pharmacological therapy", Current Medicinal Chemistry, vol. 18, No. 20, Jul. 2011, p. 3028-3034.

Shirai et al,, "New syntheses and spectral properties of pteridine-related heterocycles from 2,5-diamino-3,6-dicyanopyridine" Journal of Heterocyclic Chemistry, vol. 37, 2000, pp. 1151-1156.

Vitse et al: "New Imidazo(1,2-a)pyrazine Derivatives with Bronchodilatory and Cyclic Nucleotide Phosphodiesterase Inhibitory Activities" Bioorganic & Medicinal Chemistry, vol. 7, Jan. 1, 1999, pp. 1059-1065.

Yutilov et al., Halogenation of 2-Unsubstituted and 2-Methylimidazo[4,5-b]Pyridine Derivatives, Russian Journal of Organic Chemistry (2005), 41(3), 450-454.

Yutilov et al., Halogenation of Imidazo[4,5-b]Pyridin-2-one Derivatives, Russian Journal of Organic Chemistry (2005), 41(4), 575-579.

Zhu et al., "Synthesis of inidazo[4,5-b]quinoxaline Ribonucleosides as Linear Dimensional Analogs of Antiviral Polyhalogenated Benzimidazole Ribonucleosides" Journal of the Chinese Chemical Society, Chinese Electronic Periodical Services, China, (1998), vol. 45, No. 4, pp. 465-474.

Zinman, L., et al., "Emerging targets and treatments in amyotrophic lateral sclerosis", The Lancet Neurology, vol. 10, No. 5, May 2011, p. 481-490.

U.S. Appl. No. 12/058,127, Office Action dated May 24, 2010.

U.S. Appl. No. 12/765,820, Restriction Requirement dated Dec. 27, 2011.

U.S. Appl. No. 12/765,820, Notice of Allowance dated Jun. 14, 2012.

U.S. Appl. No. 12/765,820, Restriction Requirement dated Apr. 22, 2010.

Advisory Action for U.S. Appl. No. 12/573,730 dated Dec. 21, 2010.

Notice of Allowance for U.S. Appl. No. 11/888,902 dated Jun. 1, 2009.

Notice of Allowance for U.S. Appl. No. 12/058,127 dated Aug. 9, 2010.

Notice of Allowance for U.S. Appl. No. 12/058,127 dated Nov. 10, 2010.

Notice of Allowance for U.S. Appl. No. 12/359,186 dated Apr. 11, 2011.

Notice of Allowance for U.S. Appl. No. 12/364,394 dated Mar. 22, 2011.

(56) References Cited

OTHER PUBLICATIONS

Notice of Allowance for U.S. Appl. No. 12/573,730 dated Feb. 1, 2011.
Notice of Allowance for U.S. Appl. No. 12/165,498 dated Mar. 28, 2012.
Office Action for U.S. Appl. No. 11/888,902 dated Mar. 5, 2009.
Office Action for U.S. Appl. No. 11/888,902 dated Oct. 21, 2008.
Office Action for U.S. Appl. No. 12/058,127 dated Feb. 25, 2010.
Office Action for U.S. Appl. No. 12/165,498 dated Oct. 25, 2011.
Office Action for U.S. Appl. No. 12/359,186 dated Dec. 2, 2010.
Office Action for U.S. Appl. No. 12/573,730 dated Jul. 8, 2010.
Office Action for U.S. Appl. No. 12/573,730 dated Oct. 13, 2010.
Restriction Requirement for U.S. Appl. No. 12/058,127 dated Nov. 23, 2009.
Restriction Requirement for U.S. Appl. No. 12/359,186 dated Sep. 14, 2010.
Restriction Requirement for U.S. Appl. No. 12/364,394 dated Jan. 5, 2011.
Restriction Requirement for U.S. Appl. No. 12/573,730 dated Apr. 29, 2010.
Restriction Requirement for U.S. Appl. No. 12/765,820 dated Apr. 22, 2010.
Restriction Requirement for U.S. Appl. No. 12/519,518 dated Feb. 13, 2012.
International Search Report and Written Opinion dated Apr. 8, 2009 for PCT/US2009/000686.
International Search Report and Written Opinion dated Aug. 8, 2008 for PCT/US2007/017191.
International Search Report and Written Opinion dated Jul. 1, 2008 for PCT/US2008/004075.
International Search Report and Written Opinion dated Oct. 1, 2008 for PCT/US2007/017235.
Supplementary European Search Report for EPO Application No. 08742350.5 dated Apr. 8, 2010.
Bensimon et al., "The tolerability of riluzole in the treatment of patients with amyotrophic lateral sclerosis", Expert Opinion, Central & Peripheral Nervous Systems, Expert Opinion Drug Saf. (2004) 3(6):525-534, (11 pages).
Cudkowicz et al., "Dexpramipexole versus placebo for patients with amyotrophic lateral sclerosis (EMPOWER): a randomised, double-blind, phase 3 trial", Article, LancetNeural, www.thelancet.com/nuerology, Nov. 2013, V.12 pp. 1059-1067 (9pgs).
Lenglet et al., "A phase II_III trial of olesoxime in subjects with amyotrophic lateral sclerosis", Journal, 21: 529-536, 2014, European Journal of Neurology (8 pages).
RILUTEK® Insert. "(Riluzole) Tablets Rx Only", Prescribing Information, RILUTEK®, 2008, pp. 1-12 Sanofi-Aventis U.S. LLC (12pgs).
Riluzole [retrieved from internet on Jul. 7, 2015] <URL:http://web.archive.org/web/20090304152440/http://www.nlm.nih.gov/medlineplus/druginfo/meds/a696013.html> published on Mar. 4, 2009 as per Wayback Machine.
Riluzole Side Effects [retrieved from internet on Jul. 7, 2015] <URL:http://web.archive.org/web/20090602103354/http://www.drugs.com/sfx/riluzole-side-effects.html> published on Jun. 2, 2009 as per Wayback Machine.
Lacomblez, L. (Dec. 1996). "A Confirmatory Dose-Ranging Study of Riluzole in ALS," Neurology 47(Suppl. 4):S242-S250.
Shefner, J. et al. "Relationships Between Riluzole and Tirasemtiv Levels on Outcomes in the Benefit-ALS Trial," Cytokinetics Inc., San Francisco, CA Poster, located at <https://cytokinetics.com/wp-content/uploads/2015/10/ALSMND2014Shefner.pdf>, last visited on Jun. 7, 2017, 1 page.
$^{PR}$RILUTEK® (riluzole) (May 11, 2010). "Product Monograph," Prescribing Information, Sanofi-Aventis Canada Inc., Quebec, v3.0, submission Control No. 132512, 37 pages.
RILUTEK® (riluzole) Tablets Rx Only, Prescribing Information, located at <https://www.accessdata.fda.gov/drugsatfda_docs/label/2009/020599s011s012lbI.pdf> last visited on Jul. 11, 2017, 12 pages.
Cytokinetics, Inc. (Nov. 21, 2017). "Cytokinetics Announces Negative Results from Vitality-Als, Phase 3 Clinical Trial of Tirasemtiv in Patients with ALS Did Not Meet Primary or Secondary Endpoints Results to be Presented Dec. 8 at 28th International Symposium on ALS/MND," located at <http://ir.cytokinetics.com/news-releases/news-release-details/cytokinetics-announces-negative-results-vitality-als>, last visited on Feb. 28, 2018, 5 pages.
Notice of Allowance dated Nov. 3, 2017, for U.S. Appl. No. 14/246,230, filed Apr. 7, 2014, 9 pages.
Notice of Allowance dated Jul. 3, 2017, for U.S. Appl. No. 14/246,230, filed Apr. 7, 2014, 10 pages.
Notice of Allowance dated Jan. 31, 2017, for U.S. Appl. No. 14/246,230, filed Apr. 7, 2014, 9 pages.
Notice of Allowance dated Oct. 7, 2016, for U.S. Appl. No. 14/246,230, filed Apr. 7, 2014, 9 pages.
Notice of Allowance dated May 9, 2016, for U.S. Appl. No. 14/246,230, filed Apr. 7, 2014, 9 pages.
Notice of Allowance dated Sep. 24, 2015, for U.S. Appl. No. 14/246,230, filed Apr. 7, 2014, 10 pages.
Notice of Allowance dated Dec. 18, 2013, for U.S. Appl. No. 13/612,691, filed Sep. 12, 2012, 10 pages.
Notice of Allowance dated Jun. 27, 2012, for U.S. Appl. No. 12/780,644, filed May 14, 2010, 9 pages.
Final Office Action dated Jun. 16, 2015, for U.S. Appl. No. 14/246,230, filed Apr. 7, 2014, 9 pages.
Office Action dated Jan. 5, 2015, for U.S. Appl. No. 14/246,230, filed Apr. 7, 2014, 12 pages.
Office Action (Ex Parte Quayle) dated Oct. 10, 2013, for U.S. Appl. No. 13/612,691, filed Sep. 12, 2012, 7 pages.
Office Action dated Jun. 25, 2013, for U.S. Appl. No. 13/612,691, filed Sep. 12, 2012, 10 pages.
Office Action dated Apr. 5, 2012, for U.S. Appl. No. 13/165,281, filed Jun. 21, 2011, 8 pages.
Office Action dated Mar. 2, 2012, for U.S. Appl. No. 12/780,644, filed May 14, 2010, 9 pages.
Restriction Requirement dated Aug. 14, 2014, for U.S. Appl. No. 14/246,230, filed Apr. 7, 2014, 8 pages.
Restriction Requirement dated Mar. 25, 2013, for U.S. Appl. No. 13/612,691, filed Sep. 12, 2012, 10 pages.
Restriction Requirement dated Jul. 16, 2008, for U.S. Appl. No. 11/888,902, filed Aug. 1, 2007, 10 pages.
Restriction Requirement dated Aug. 3, 2011, for U.S. Appl. No. 12/165,498, filed Jun. 30, 2008, 6 pages.
Restriction Requirement dated Apr. 15, 2011, for U.S. Appl. No. 12/165,498, filed Jun. 30, 2008, 9 pages.
Restriction Requirement dated Jan. 6, 2012, for U.S. Appl. No. 12/780,644, filed May 14, 2010, 8 pages.
Notice of Allowance dated Aug. 8, 2018, for U.S. Appl. No. 14/246,230, filed Apr. 7, 2014, 9 pages.
Notice of Allowance dated Mar. 26, 2018, for U.S. Appl. No. 14/246,230, filed Apr. 7, 2014, 9 pages.

* cited by examiner

COMBINATION ALS THERAPY

This application claims the benefit under 35 U.S.C. § 371 of PCT International Application No. PCT/US2012/046523, filed Jul. 12, 2012, which in turn claims the benefit of priority to U.S. Application Nos. 61/507,381, filed Jul. 13, 2011, 61/637,770, filed Apr. 24, 2012, 61/544,533, filed Oct. 7, 2011; 61/646,699, filed May 14, 2012, and 61/637,759, filed Apr. 24, 2012, each of which is incorporated by reference for all purposes.

Amyotrophic lateral sclerosis (ALS) is a degenerative and progressive disorder of the nervous system. ALS is characterized by progressive loss of motor neurons in the lateral column of the spinal cord and/or motor cortex. With progressive loss of motor neurons, the innervation to skeletal muscle is lost which results in an inability to ambulate, conduct daily activities and affects swallowing and breathing. ALS is a rare and usually fatal disease; its progression can be variable but on average patients end up dying within 3 years of diagnosis. Most patients succumb to respiratory failure with broncho-pneumonia and pneumonia as the main causes of death. Treatment is supportive because no curative treatment exists.

Riluzole currently is the only drug approved to treat ALS. While the exact mechanism of action of riluzole is unknown, it is believed to act by inhibiting the deleterious effects of an overload of glutamic acid and other neurotransmitters in the central nervous system (see, e.g., Couratier et al., *NeuroReport* (1994), 5(8):1012-14; Estevez et al., *Eur. J. Pharmacol.* (1995), 280(1): 47-53; Rothstein et al., *J. Neorochem.* (1995), 65(2): 643-51). Studies have shown that the serum and plasma concentrations of riluzole vary greatly from person to person (see, e.g., Groeneveld et al., *J. Neurol. Sci.* (2001), 191: 310-13). Such variability can lead to difficulties in determining and delivering a therapeutically effective dose to a patient and may affect the incidence and severity of adverse events (see, e.g., Groeneveld et al., *Neurology* (2003), 61: 1141-43).

6-Ethynyl-1-(pentan-3-yl)-1H-imidazo[4,5-b]pyrazin-2 (3H)-one (also known as CK-2017357 or CK-357) is a selective activator of the fast skeletal muscle troponin complex, which sensitizes fast skeletal muscle to calcium and results in an amplification of the response to neuromuscular input, an increase in muscle power, and a decrease in the fatigability of muscle (see, e.g., U.S. Pat. No. 7,598,248). The use of CK-2017357 is being studied for use in the treatment of patients with ALS. By increasing the contractile force developed by fast skeletal muscle fibers in response to any level of neuronal input, treatment with CK-2017357 may improve activities of daily living (such as ambulation, breathing and feeding), reduce hospitalizations, and possibly prolong the survival of patients with ALS.

CK-2017357 has been shown to be a mechanism-based inhibitor of human CYP1A2 in vitro, with a $K_1$ (inactivation constant) of 1.9 μM and $k_{inact}$ (max rate constant for inactivation) of 0.031 $min^{-1}$. In humans, riluzole is primarily metabolized by CYP1A2 (see, e.g., Sanderink et al., *J. Pharmacol. & Exp. Ther.* (1997), 282(3): 1465-72). A number of other drugs have been assessed for their ability to inhibit the metabolism of riluzole by human hepatic microsomes in vitro; although inhibition has been observed in some cases (e.g., amitriptyline, diclofenac, diazepam, nicergoline, clomipramine, imipramine), the high concentrations required for inhibition make it unlikely that these drugs would alter riluzole concentrations if used in combination with riluzole in the clinical setting (see Bensimon et al., *Expert Opin. Drug Saf.* (2004), 3(6): 525-34).

Provided is a method for treating ALS in a subject, comprising administering to the subject a therapeutically effective amount of riluzole and a therapeutically effective amount of CK-2017357.

Also provided is a method for reducing the variability of riluzole exposure (e.g., $C_{max}$ and/or $AUC_{24h}$) in a subject, comprising administering to the subject a therapeutically effective amount of CK-2017357.

Also provided is a method for reducing the variability of riluzole exposure (e.g., $C_{max}$ and/or $AUC_{24h}$) between two or more subjects, comprising administering to the subjects a therapeutically effective amount of CK-2017357.

Also provided is a method of increasing the exposure of riluzole (e.g., $C_{max}$ and/or $AUC_{24h}$) in a subject, comprising administering to the subject a therapeutically effective amount of CK-2017357.

Also provided is a method of increasing the half-life of riluzole in a subject, comprising administering to the subject a therapeutically effective amount of CK-2017357.

Also provided is a method for decreasing the frequency of riluzole dosing in the subject, comprising administering to the subject a therapeutically effective amount of CK-2017357.

Also provided is a method for decreasing the total daily dose of riluzole in a subject, comprising administering to the subject a therapeutically effective amount of CK-2017357.

Also provided is a method for reducing the incidence and/or severity of adverse events in a subject treated with riluzole, comprising administering to the subject treated with riluzole a therapeutically effective amount of CK-2017357.

Also provided is a pharmaceutical composition comprising a therapeutically effective amount of riluzole and a therapeutically effective amount of CK-2017357.

Also provided is a method for treating ALS in a subject, comprising administering to the subject at least two doses daily of CK-2017357.

Figure 1:
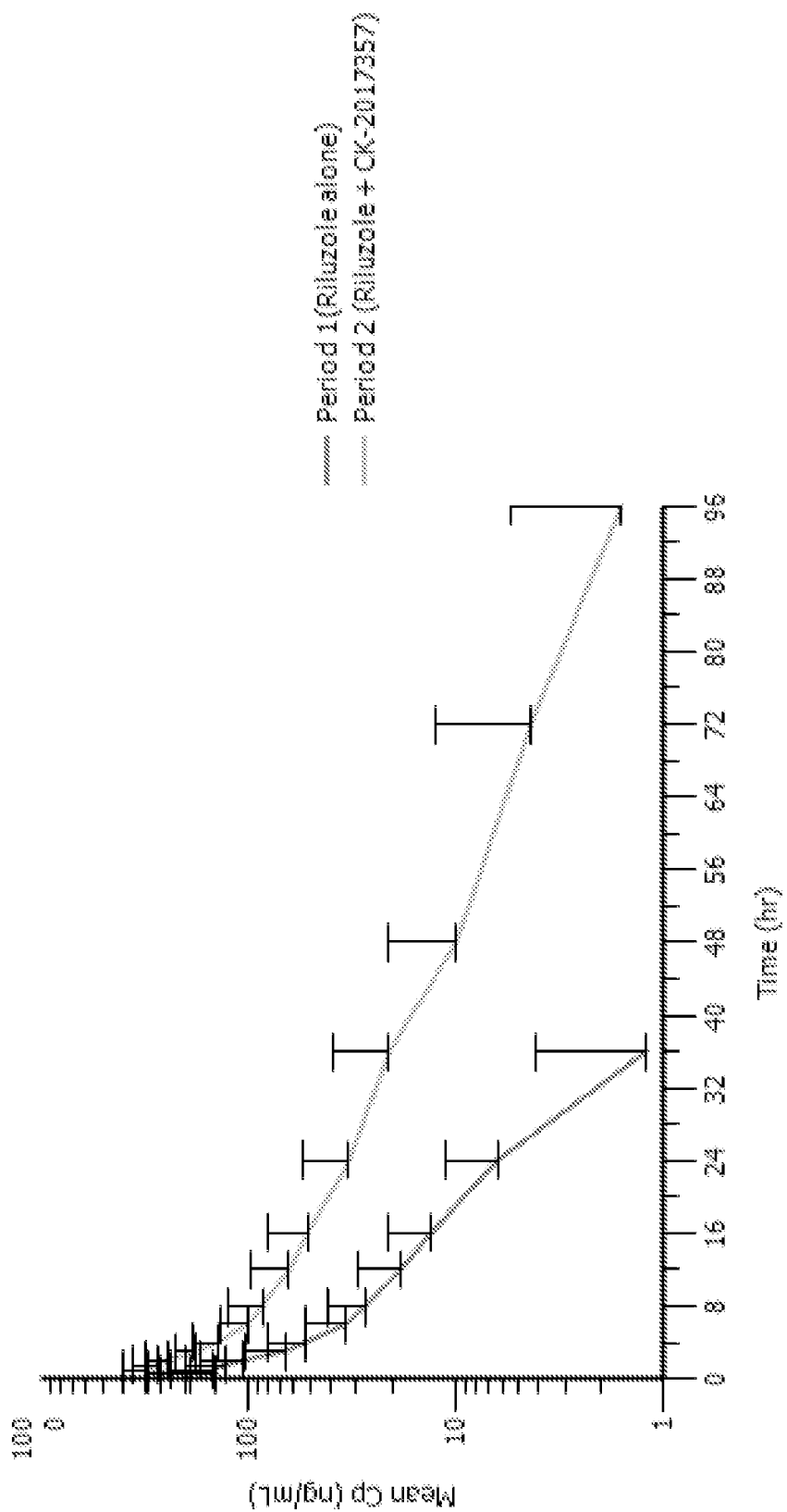
FIG. 1 provides mean riluzole plasma concentration as a function of time for riluzole alone (50 mg single dose) and riluzole (50 mg single dose) and CK-2017357 (250 mg daily×11 days in healthy subjects.

As used herein, the following abbreviations, words and phrases are generally intended to have the meanings as set forth below, except to the extent that the context in which they are used indicates otherwise.

As used herein, $AUC_{24h}$ is the area under the plasma concentration-time curve from hour 0 to the last measurable plasma concentration (e.g., 24 hours), calculated by the linear trapezoidal rule.

As used herein, ALS or amyotrophic lateral sclerosis refers to the motor neuron disease commonly known as Lou Gehrig's Disease, and in some embodiments, amyotrophic lateral sclerosis with early bulbar involvement or the bulbar form of the disease, and in some embodiments, "limb-onset" ALS.

As used herein, QD refers to once a day.

As used herein, BID refers to twice a day.

As used herein, $C_{max}$ refers to maximum plasma concentration

As used herein, fm refers to fraction metabolized.

Provided is a method for treating ALS in a subject, comprising administering to the subject a therapeutically effective amount of riluzole and a therapeutically effective amount of CK-2017357.

In some embodiments, administering the riluzole in combination with CK-2017357 extends survival and/or time to tracheostomy.

In some embodiments, the therapeutically effective amount of riluzole administered in combination with CK-2017357 is a smaller dose than the therapeutically effective amount of riluzole when administered singly (i.e., without CK-2017357 treatment). In some embodiments, both the therapeutically effective amount of riluzole and the therapeutically effective amount of CK-2017357 when administered in combination are smaller doses than the therapeutically effective amount of riluzole and the therapeutically effective amount of CK-2017357 when each is administered singly.

In some embodiments, the administration of riluzole is BID. In some embodiments, the administration of riluzole is QD.

In some embodiments, the administration of CK-2017357 is BID. In some embodiments, the administration is QD.

In some embodiments, the administration of riluzole is QD and the administration of CK-2017357 is BID. In some embodiments, the administration of riluzole is BID and the administration of CK-2017357 is BID.

In some embodiments, the administration of riluzole is QD and the administration of CK-2017357 is QD. In some embodiments, the administration of riluzole is BID and the administration of CK-2017357 is QD.

In some embodiments, the CK-2017357 is administered in two or more doses at different times (e.g., once in the morning and once in the evening). In some embodiments, the CK-2017357 is administered in two or more equal doses. In some embodiments, the CK-2017357 is administered in two or more different doses. In some embodiments, the dose of CK-2107357 is titrated over time to a different (e.g., higher) daily dose level.

In some embodiments, single daily dose of 50 mg riluzole is administered in combination with a therapeutically effective amount of CK-2017357. In some embodiments, a single daily dose of 50 mg riluzole is administered in combination with a total daily dose of between about 125 mg and 2000 mg of CK-2017357. In some embodiments, a single daily dose of 50 mg riluzole is administered in combination with a total daily dose of 125, 250, 375, or 500 mg of CK-2017357.

In some embodiments, a twice daily dose of 25 mg riluzole is administered in combination with a therapeutically effective amount of CK-2017357. In some embodiments, a twice daily dose of 25 mg riluzole is administered in combination a total daily dose of between about 125 mg and 2000 mg of CK-2017357. In some embodiments, a twice daily dose of 25 mg riluzole is administered in combination with a total daily dose of 125, 250, 375, or 500 mg of CK-2017357.

In some embodiments, a single daily dose of 25 mg riluzole is administered in combination with a therapeutically effective amount of CK-2017357. In some embodiments, a single daily dose of 25 mg riluzole is administered in combination with a total daily dose of between about 125 mg and 2000 mg of CK-2017357. In some embodiments, a single daily dose of 25 mg riluzole is administered in combination with a total daily dose of 125, 250, 375, or 500 mg of CK-2017357.

In some embodiments, a twice daily dose of 12.5 mg riluzole is administered in combination with a therapeutically effective amount of CK-2017357. In some embodiments, a twice daily dose of 12.5 mg riluzole is administered in combination with a total daily dose of between about 125 mg and 2000 mg of CK-2017357. In some embodiments, a twice daily dose of 12.5 mg riluzole is administered in combination with 125, 250, 375, or 500 mg of CK-2017357.

Also disclosed is a method for increasing the half-life of riluzole in a subject, comprising administering to the subject a therapeutically effective amount of CK-2017357.

Also disclosed is a method for decreasing the frequency of riluzole dosing in a subject (e.g., from twice-daily to once-daily) or reducing the dose of riluzole administered to the subject (e.g., from 200 mg daily to 100 mg daily, or from 100 mg daily to 50 mg daily, or from 50 mg daily to 25 mg daily).

Also disclosed is a method for reducing the inter-subject variability of riluzole exposure (e.g., $C_{max}$ and/or $AUC_{24h}$) between two or more subjects, comprising administering to the subjects a therapeutically effective amount of CK-2017357.

Also disclosed is a method for reducing the intra-subject variability of riluzole exposure (e.g., $C_{max}$ and/or $AUC_{24h}$), comprising administering to the subject a therapeutically effective amount of CK-2017357.

Also disclosed is a method for reducing the incidence and/or severity of adverse events in a subject treated with riluzole, comprising administering to the subject a therapeutically effective amount of CK-2017357. In some embodiments, the adverse event is a CNS-related adverse event (see, e.g., Mashiro et al., *Anesthesia & Analgesia* (2007), 104:1415-21).

In some embodiments, CK-2017357 is administered to the subject concurrently with riluzole administration, i.e., CK-2017357 and riluzole are administered simultaneously, essentially simultaneously or within the same treatment protocol. In some instances of concurrent administration, administration of CK-2017357 and riluzole begin and end at the same time (i.e., on the same day or within the same treatment protocol). In other instances of concurrent administration, only one of CK-2017357 and riluzole is administered for a first period of time, followed by co-administration of the CK-2017357 and riluzole for a second period of time. For example, the subject may receive riluzole for a first period of time, then receive both CK-2017357 and riluzole for a second period of time. Administration of either CK-2017357 or riluzole may then continue for a third period of time. In another example, the subject may receive CK-2017357 for a first period of time, then receive both CK-2017357 and riluzole for a second period of time. Administration of either CK-2017357 or riluzole may then continue for a third period of time. In other instances of concurrent administration, CK-2017357 and riluzole are co-administered for a first period of time, followed by administration of only one of CK-2017357 and riluzole for a second period of time. For example, the subject may receive both CK-2017357 and riluzole for a first period of time, then receive CK-2017357 for a second period of time. In another example, the subject may receive both CK-2017357 and riluzole for a first period of time, then receive riluzole for a second period of time. In all instances, alternate administration may be repeated during a single treatment protocol. The determination of the order of administration and the number of repetitions of administration of each therapy during a treatment protocol is within the knowledge of the skilled physician after evaluation of the condition of the patient.

In some embodiments, riluzole and CK-2017357 are administered sequentially. In some instances of sequential administration, CK-2017357 is administered to the subject after riluzole administration has ended. The administration of CK-2017357 may begin immediately following termination of riluzole administration, or there may be a time interval (e.g., one day, one week, one month, six months, one year, etc.) between the end of riluzole administration and the beginning of CK-2017357 administration. In other instances of sequential administration, riluzole is administered to the subject after CK-2017357 administration has ended. The administration of riluzole may begin immediately following termination of CK-2017357 administration, or there may be a time interval (e.g., one day, one week, one month, six months, one year, etc.) between the end of CK-2017357 administration and the beginning of riluzole administration. In each instance, alternate administration may be repeated during a single treatment protocol. The determination of the order of administration and the number of repetitions of administration of each therapy during a treatment protocol is within the knowledge of the skilled physician after evaluation of the condition of the patient.

In some embodiments, CK-2017357 and riluzole are administered in a single pharmaceutical composition. The single pharmaceutical composition may be administered via any of the accepted modes of administration for therapeutic agents including, but not limited to, orally, sublingually, subcutaneously, intravenously, intranasally, topically, transdermally, intraperitoneally, intramuscularly, intrapulmonarily, vaginally, rectally, or intraocularly. In some embodiments, the single pharmaceutical composition is administered orally. In some embodiments, the single pharmaceutical composition is formulated to administer both CK-2017357 and riluzole at the same time or rate. In some embodiments, the single pharmaceutical composition is formulated to administer both CK-2017357 and riluzole at different times or rates. For example, the single pharmaceutical composition may deliver riluzole at a slower rate the CK-2017357, or CK-2017357 at a slower rate than riluzole. In another example, the single pharmaceutical composition may deliver CK-2017357 first followed by riluzole (i.e., delayed release of riluzole), or riluzole first followed by CK-2017357 (i.e., delayed release of CK-2017357).

In some embodiments, CK-2017357 and riluzole are administered in separate pharmaceutical compositions. Each agent may, because of different physical and chemical characteristics, be administered by different routes. For example, one agent can be administered orally, while the other is administered intravenously. Alternatively, each agent may be administered by the same route. For example, both CK-2017357 and riluzole may be administered orally (i.e., in the form of two separate pills or capsules). The determination of the mode of administration and the advisability of administration, in the same pharmaceutical composition (if possible) is within the knowledge of the skilled clinician. The initial administration can be made according to established protocols known in the art, and then, based upon the observed effects, the dosage, modes of administration and times of administration can be modified by the skilled clinician.

Also provided is a method for treating ALS by administering to a patient at least two doses daily of CK-2017357. In some embodiments, two doses of CK-2017357 are administered at different times (e.g., once in the morning and once in the evening). In some embodiments, the total daily dose is at least about 250 mg, or at least about 300 mg, or at least about 350 mg, or at least about 400 mg, or at least about 450 mg, or at least about 500 mg. In some embodiments, at least one of the doses is equal to or greater than about 125 mg, or equal to or greater than about 150 mg, or equal to or greater than about 200 mg, or equal to or greater than about 250 mg. In some embodiments, at least two of the doses are equal to or greater than about 125 mg, or equal to or greater than about 150 mg, or equal to or greater than about 200 mg, or equal to or greater than about 250 mg. In some embodiments, the CK-2017357 is administered in two or more equal doses (e.g., two equal doses of 125 mg or two equal doses of 250 mg). In some embodiments, the CK-2017357 is administered in two or more different doses (e.g., 125 mg/250 mg or 250 mg/125 mg). In some embodiments, the dose of CK-2107357 is titrated over time to a different (e.g., higher) daily dose level.

Administration of CK-2017357 can be via any of the accepted modes of administration for therapeutic agents including, but not limited to, orally, sublingually, subcutaneously, intravenously, intranasally, topically, transdermally, intraperitoneally, intramuscularly, intrapulmonarily, vaginally, rectally, or intraocularly. In some embodiments, CK-2017357 is administered orally. In other embodiments, CK-2017357 is administered intravenously. In still other embodiments, CK-2017357 is administered into the lungs by inhalation or spraying of a dry powder, suspension, solution or aerosol comprising CK-2017357.

Pharmaceutically acceptable compositions include solid, semi-solid, liquid and aerosol dosage forms, such as, e.g., tablets, capsules, powders, liquids, suspensions, suppositories, aerosols or the like. CK-2017357 can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

CK-2017357 can be administered either alone or in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95% or, in certain embodiments, about 0.5% to 50% by weight of CK-2017357. Actual methods of preparing such dosage forms are known, or will be apparent, to those skilled in this art; for example, see *Remington's Pharmaceutical Sciences*, Mack Publishing Company, Easton, Pa.

In certain embodiments, the compositions will take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In certain embodiments of a solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. the active ingredient and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of CK-2017357 contained in such parenteral compositions is dependent on the specific nature of the compound, as well as the activity of CK-2017357 and the needs of the subject. In some embodiments, percentages of active ingredient of 0.01% to 10% in solution are employable, and may be higher if the composition is a solid which will be subsequently diluted.

Pharmaceutical compositions of CK-2017357 may also be administered to the respiratory tract as an aerosol or solution for a nebulizer, or as a microfine powder for insufflation, alone or in combination with an inert carrier such as lactose. In some embodiments, the particles of the pharmaceutical composition have diameters of less than 50 microns, in certain embodiments, less than 10 microns.

Example 1: Effect of Multiple Daily Doses of CK-2017357 on the PK of a Single Dose of Riluzole in Healthy Subjects The primary objective of this study was to evaluate the effect of multiple daily doses of CK-2017357 on the pharmacokinetics (PK) of a single dose of riluzole in healthy subjects. On Day 1, 12 subjects (7 males and 5 females) received a single 50 mg oral dose of riluzole. On Day 6, all subjects began 11 days of oral dosing with 250 mg CK-2017357 QD (through Day 16). On Day 13, 11 of the 12 subjects received another single 50 mg oral dose of riluzole. Following each dose of riluzole, plasma samples were collected at pre-dose, 0.5, 1, 1.5, 2, 3, 4, 6, 8, 12, 16, 24, 36, 48, 72, and 96 hours post-dose. Plasma concentrations of riluzole were determined using a validated HPLC/MS/MS method with a quantitation range of 5.00 to 2,000 ng/mL. Samples were analyzed using a 50.0 µL aliquot volume and a protein-precipitation extraction procedure followed by HPLC/MS/MS. Riluzole concentrations were calculated with a $1/x^2$ linear regression over a concentration range of 5.00 to 2,000 using riluzole-$^{13}$C,$^{15}$N$_2$ as an internal standard. Separately, another set of plasma samples were collected at pre-dose of CK-2017357 on days 11, 12, and 13. These plasma samples were analyzed using a validated LC/MS/MS method for trough CK-2017357 levels to determine the attainment of steady-state pharmacokinetics of CK-2017357.

Plasma concentration data of riluzole were analyzed by non-compartmental methods to determine pharmacokinetic parameters of riluzole. Descriptive pharmacokinetic parameters such as Cmax, Tmax, AUC, t1/2, Cl/F, and V/F were calculated using Phoenix WinNonlin 6.1 (Pharsight, Mountain View, Calif.). All concentrations <LLOQ were set to zero for the purpose of calculating descriptive statistics and noncompartmental analysis. Summary PK parameters of riluzole are presented in Tables 1A and 1B below.

TABLE 1A

Summary pharmacokinetic parameters of riluzole in healthy subjects

|  | $C_{max}$ (ng/ml) | $T_{max}$ (hr) | $AUC_{last}$ (hr*ng/ml) | $AUC_{inf}$ (hr*ng/ml) | $t_{1/2}$ (hr) | CL/F (ml/hr) |
|---|---|---|---|---|---|---|
| N | 12 | 12 | 12 | 12 | 12 | 12 |
| Mean | 190 | 1.1 | 766 | 845 | 8.0 | 86258 |
| SD | 113 | 0.5 | 416 | 440 | 2.5 | 75198 |
| Min | 49 | 0.5 | 138 | 163 | 2.6 | 29859 |
| Median | 202 | 1.3 | 633 | 722 | 8.0 | 70415 |
| Max | 416 | 2.0 | 1534 | 1675 | 11.0 | 307213 |
| CV % | 59.6 | 46.9 | 54.4 | 52.1 | 31.7 | 87.2 |

TABLE 1B

Summary pharmacokinetic parameters of riluzole + CK2017357 (250 mg QD) in healthy subjects

|  | $C_{max}$ (ng/ml) | $T_{max}$ (hr) | $AUC_{last}$ (hr*ng/ml) | $AUC_{inf}$ (hr*ng/ml) | $t_{1/2}$ (hr) | CL/F (ml/hr) |
|---|---|---|---|---|---|---|
| N | 11 | 11 | 11 | 11 | 11 | 11 |
| Mean | 323 | 1.2 | 2761 | 2929 | 15.5 | 20696 |
| SD | 87 | 0.6 | 1534 | 1601 | 5.0 | 8321 |
| Min | 191 | 0.5 | 1309 | 1412 | 9.6 | 7124 |
| Median | 324 | 1.0 | 2443 | 2559 | 14.9 | 19535 |
| Max | 482 | 2.0 | 6613 | 7019 | 23.2 | 35410 |
| CV % | 27.0 | 46.0 | 55.6 | 54.7 | 32.2 | 40.2 |

Figure 2:
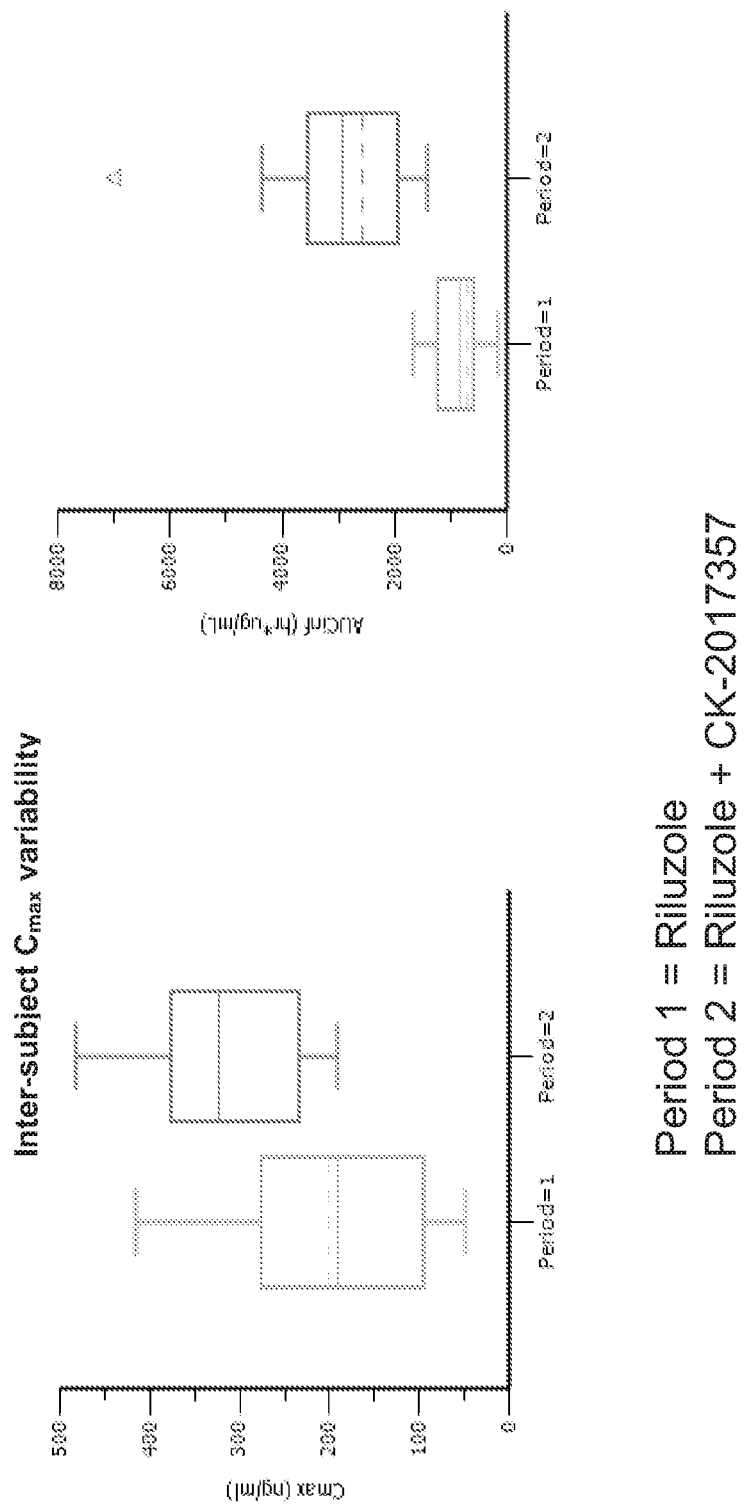
FIG. 2 illustrates the effect of steady-state CK-2017357 on riluzole pharmacokinetics in healthy subjects. Panel A provides $C_{max}$ for riluzole alone (50 mg single dose) and riluzole (50 mg single dose)+CK-2017357 (250 mg daily for 11 days). Panel B provides $AUC_{inf}$ for riluzole alone (50 mg single dose) and riluzole (50 mg single dose)+CK-2017357 (250 mg daily for 11 days). The figure shows that in healthy subjects, the inter-subject variability of $C_{max}$ of riluzole has been reduced through co-administration of CK-2017357.

The extent of drug-drug interaction was assessed by comparing $AUC_{inf}$ values from Period 1 (riluzole alone) to values from Period 2 (riluzole+CK-2017357). Results of this study are presented in Table 2 below. Mean plasma concentration-time profiles are presented graphically in FIG. 1, and $C_{max}$ and $AUC_{inf}$ data for Periods 1 and 2 are represented in FIG. 2.

TABLE 2

Individual and Summary of $AUC_{inf}$-fold increase of riluzole in the presence of steady-state CK-2015375 (250 mg) in healthy subjects

| Patient | AUCinf Period 1 (hr*ng/ml) | AUCinf Period 2 (hr*ng/ml) | Fold increase |
|---|---|---|---|
| 1 | 1335.38 | | |
| 2 | 813.03 | 1622.66 | 2.00 |
| 3 | 619.77 | 1931.23 | 3.12 |
| 4 | 162.75 | 1951.67 | 11.99 |
| 5 | 883.12 | 2608.46 | 2.95 |
| 6 | 1189.32 | 4361.09 | 3.67 |
| 7 | 1674.53 | 3577.29 | 2.14 |
| 8 | 1263.88 | 7018.50 | 5.55 |
| 9 | 630.27 | 2635.93 | 4.18 |
| 10 | 573.21 | 2559.42 | 4.47 |
| 11 | 378.92 | 1412.02 | 3.73 |
| 12 | 612.18 | 2540.58 | 4.15 |
| N | 12 | 11 | 11 |
| Mean | 844.70 | 2929.00 | 4.36 |
| SD | 440.32 | 1600.93 | 2.73 |
| Min | 162.75 | 1412.02 | 2.00 |
| Median | 721.65 | 2559.42 | 3.73 |
| Max | 1674.53 | 7018.50 | 11.99 |
| CV % | 52.1 | 54.7 | 62.7 |

This study showed that steady-state CK-2017357 (250 mg) raised the mean $C_{max}$ of riluzole approximately 1.7-fold, and its mean $AUC_{inf}$ approximately 4.4-fold compared with riluzole alone. The mean $t_{1/2}$ of riluzole increased from 8.0 hours to 15.5 hours in the presence of steady-state CK-2017357. As illustrated in FIG. 2, co-administration of CK-2017357 generally reduced the inter-subject variability of riluzole pharmacokinetics in these healthy subjects.

Example 2: Drug-Drug Interaction (DDI) Between Riluzole and CK-2017357 in ALS Patients This was a placebo controlled, three-period crossover study. Each patient received 50 mg riluzole BID and single doses of placebo, 250 mg CK-2017357, and 500 mg CK-2017357 in random order, separated by 6-10 days. Duplicate PK samples were collected from each patient in the clinical study. One set was analyzed for CK-2017357, and the other analyzed for riluzole using a validated LC/MS/MS method. Riluzole exposure ($AUC_{24h}$) was calculated for each patient and each treatment of CK-2015357 (placebo, 250 mg, and 500 mg). Riluzole AUC-fold increase over CK-2017357 placebo period was used to assess the extent of drug-drug interaction.

Plasma concentrations of riluzole were determined using a validated HPLC/MS/MS method with a quantitation range of 5.00 to 2,000 ng/mL. Samples were analyzed using a 50.0 μL aliquot volume and a protein-precipitation extraction procedure followed by HPLC/MS/MS. Riluzole concentrations were calculated with a $1/x^2$ linear regression over a concentration range of 5.00 to 2,000 using riluzole-$^{13}C,^{15}N_2$ as an internal standard. Descriptive pharmacokinetic parameters such as $C_{max}$, $T_{max}$, AUG, $t_{1/2}$, Cl/F, and V/F were calculated using Phoenix WinNonlin 6.1 (Pharsight, Mountain View, Calif.). All concentrations <LLOQ were set to zero for the purpose of calculating descriptive statistics and noncompartmental analysis. Since the time of dosing for riluzole was not recorded, time elapsed was calculated based on nominal time points of CK-2017357, and used to calculate riluzole $AUG_{24h}$.

Figure 3:
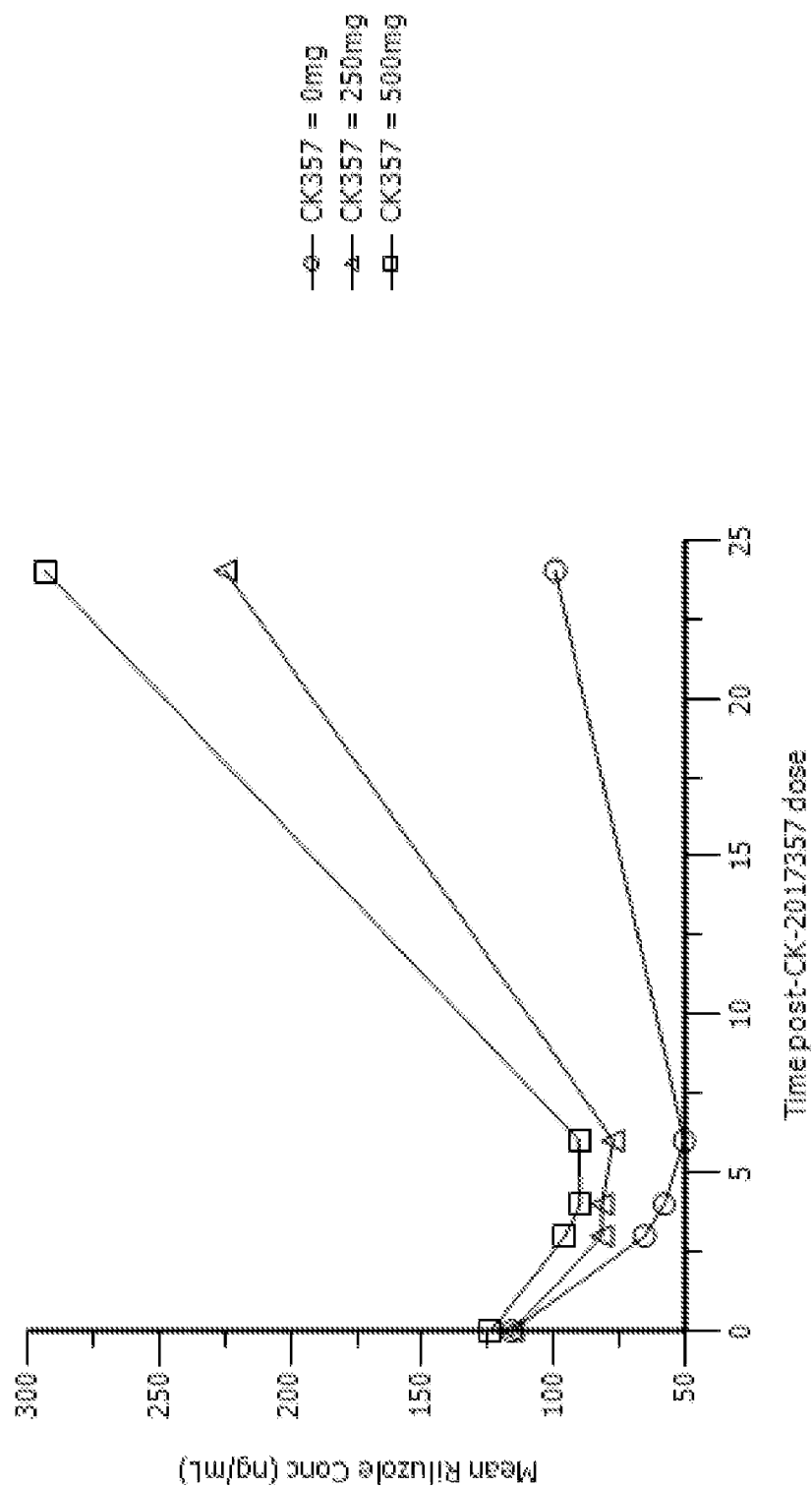
FIG. 3 provides mean riluzole plasma concentration as a function of time for 50 mg riluzole administered BID and CK-2017357 administered at either 250 or 500 mg single dose in ALS patients.

The results of this experiment are summarized in Table 3 below and mean plasma concentration-time profiles are presented in FIG. 3.

TABLE 3

Individual and summary riluzole $AUC_{24\,h}$ and $AUC_{24\,hr}$-fold increase following oral riluzole at 50 mg b.i.d.

| Patient | CK357 = 0 mg (hr*ng/ml) | CK357 = 250 mg (hr*ng/ml) | CK357 = 500 mg (hr*ng/ml) | $AUC_{24\,hr}$-fold Increase (CK-357 = 250 mg) | $AUC_{24\,hr}$-fold Increase (CK-357 = 500 mg) |
|---|---|---|---|---|---|
| 1 | 2831.49 | 4453.07 | 4062.97 | 1.57 | 1.43 |
| 2 | 1093.68 | 2457.77 | 2346.72 | 2.25 | 2.15 |
| 3 | | | 4778.27 | | |
| 4 | 2492.82 | 3767.26 | 4082.12 | 1.51 | 1.64 |
| 5 | 307.49 | | | | |
| 6 | 829.77 | 5034.99 | 4510.3 | 6.07 | 5.44 |
| 7 | 747.85 | 1828.87 | 2623.22 | 2.45 | 3.51 |
| 8 | 2540.48 | 1841.12 | 5652.57 | 0.72 | 2.23 |
| 9 | 945.95 | 1761.84 | 4024.18 | 1.86 | 4.25 |
| 10 | 1400.63 | 2509.68 | 7921.64 | 1.79 | 5.66 |
| 11 | 1263.74 | 4464.6 | | | 3.53 |
| 12 | 992.23 | 2194.64 | 3132.45 | 2.21 | 3.16 |
| 13 | 2172.04 | 4805.42 | 5410.5 | 2.21 | 2.49 |
| 14 | 2220.49 | 3939.67 | 5655.82 | 1.77 | 2.55 |
| 15 | 2647.84 | 1850.43 | 2055.75 | 0.70 | 0.78 |
| 16 | 1125.41 | 2947.04 | 3972.68 | 2.62 | 3.53 |
| 17 | 1837.04 | 1564.05 | 5600.95 | 0.85 | 3.05 |
| 18 | 3047.02 | 7371.82 | 7084.32 | 2.42 | 2.33 |
| 19 | 1155.09 | 4366.21 | 3438.4 | 3.78 | 2.98 |
| 20 | 2699.12 | 3939.62 | 4753.02 | 1.46 | 1.76 |
| 21 | 683.16 | 4034.31 | 4295.43 | 5.91 | 6.29 |
| 22 | 1511.98 | 4806.32 | 2986.23 | 3.18 | 1.98 |
| 23 | 2087.11 | 3828.63 | 2197.83 | 1.83 | 1.05 |
| 24 | 1384.24 | | | | |
| 25 | 2003.85 | 2644.38 | 2773.55 | 1.32 | 1.38 |
| 26 | 1477.45 | 2971.36 | 3945.65 | 2.01 | 2.67 |
| 27 | 4116.82 | 4620.8 | 5254.25 | 1.12 | 1.28 |
| 28 | 1460.67 | 2136.77 | 3992.31 | 1.46 | 2.73 |
| 29 | 2344.66 | 2437.78 | 3888.27 | 1.04 | 1.66 |
| 30 | 2083.63 | 1598.71 | 5707.86 | 0.77 | 2.74 |
| 31 | 996.99 | 1250.21 | 830.83 | 1.25 | 0.83 |
| 32 | 2569.22 | 3265.26 | 4360.36 | 1.27 | 1.70 |
| 33 | | 4171.45 | 3685.49 | | |
| 34 | 4841.83 | 5862.48 | 9116.2 | 1.21 | 1.88 |
| 35 | 1163.34 | 4568.86 | 3138.61 | 3.93 | 2.70 |
| 36 | 838.09 | 2295.37 | 3604.97 | 2.74 | 4.30 |
| 37 | 2812.13 | 4350.55 | 4292.15 | 1.55 | 1.53 |
| 38 | 1438.58 | 3730.11 | 4386.6 | 2.59 | 3.05 |
| 39 | | | 3547.69 | | |
| 40 | 1158.27 | 1575.61 | 1817.17 | 1.36 | 1.57 |
| 41 | 1387.18 | 887.4 | 3869.44 | 0.64 | 2.79 |
| 42 | 536.67 | 1448.56 | 849.78 | 2.70 | 1.58 |
| 43 | | | 1379.36 | | |
| N | 39 | 38 | 40 | 37 | 36 |
| Mean | 1775.54 | 3252.18 | 4025.65 | 2.10 | 2.57 |
| SD | 969.09 | 1462.15 | 1721.25 | 1.27 | 1.32 |
| Min | 307.49 | 887.4 | 830.83 | 0.64 | 0.78 |
| Median | 1460.67 | 3118.31 | 3982.49 | 1.79 | 2.41 |
| Max | 4841.83 | 7371.82 | 9116.2 | 6.07 | 6.29 |
| CV % | 54.6 | 45 | 42.8 | 60.5 | 51.1 |

Analysis of riluzole $AUC_{24h}$ following 50 mg BID showed a general trend of increasing riluzole concentrations in CK-2017357 active periods (250 and 500 mg vs. 0 mg). Compared to the CK-2017357 placebo period, mean riluzole $AUC_{24h}$ increased approximately 2.1- and 2.6-fold for the 250- and 500-mg CK-2017357 dose, respectively. As illustrated in FIG. 3, the mean riluzole $C_{max}$ roughly doubled in the presence of steady-state concentrations of CK-2017357.

Example 3: Pharmacokinetics and Interactive Effects of the Fast Skeletal Muscle Activator CK-2017357 and Riluzole The objective of this study was to determine the pharmacokinetics of repeated doses of CK-2017357 both in the presence and absence of riluzole, and to determine the effects of CK-2017357 at varying doses on plasma riluzole serum levels.

In this study, 49 patients with ALS were treated; 24 patients were not taking riluzole and the remainder took a stable but reduced dose of riluzole (50 mg daily). Patients (n=off/on riluzole) received single daily doses of placebo (n=6/7), 125, 250, or 375 mg of CK-357 (n=6/6 for all 3 CK-2017357 groups) for 14 days. CK-2017357 and riluzole levels were measured on Days 1, 2, 8 and 15.

Plasma levels of CK-2017357 achieved steady state by Day 8; levels four hours after dosing on Day 8 were approximately 70% higher than four hours after the first dose on Day 1. CK-2017357 $C_{max}$ increased proportionally by dose with no apparent effect of riluzole, as shown in Table 4.

TABLE 4

CK-2017357 $C_{max}$ levels with and without riluzole

| CK-2017357 Daily Dose | CK-2017357 Cmax (mcg/mL) | |
|---|---|---|
| | No Riluzole | On Riluzole |
| 125 | 4.1 | 6.0 |
| 250 | 7.4 | 8.4 |
| 375 | 12.7 | 13.5 |

CK-2017357 approximately doubled riluzole levels across all dose groups as shown in Table 5 below Adverse event frequencies were not altered by the presence of riluzole at any dose of CK-2017357.

TABLE 5

Riluzole $C_{max}$ levels with various doses of CK-2017357

| Dose Group | $C_{max}$ (ng/mL) Median ± SD | $AUC_{last}$ (hr*μg/mL) Median ± SD |
|---|---|---|
| Placebo | 120 ± 40 | 20.0 ± 8.3 |
| 125 mg once daily | 243 ± 89 | 42.6 ± 14.8 |
| 250 mg once daily | 143 ± 125 | 30.0 ± 21.7 |
| 375 mg once daily | 228 ± 169 | 46.3 ± 18.2 |

CK-2017357 had predictable linear kinetics at the repeated doses used in the current study, reaching steady state within 1 week. CK-2017357 plasma levels were not affected by the presence of riluzole. Riluzole levels were increased by CK-2017357 with plasma levels increasing approximately 2-fold across all dose levels of CK-2017357. However, no adverse events were reported during this study attributable to higher riluzole levels with the daily riluzole dose reduced to 50 mg daily. These results suggest that CK-2017357 and riluzole may be given safely in combination.

Example 4: Investigation of Twice-Daily Dose Titration Regimen of CK-2017357 in Patients with ALS In previous clinical experiments, 1-(ethylpropyl)-6-ethynylimidazo[4,5-b]pyrazin-2-ol (CK-2017357) has been administered once a day in the morning. While improvements in patient and investigator global assessments, muscle fatigability and pulmonary function have been observed in these studies, dizziness has been a dose-limiting adverse event in both healthy volunteers and in patients with ALS. This example examines whether the maximum tolerable total daily dose of CK-2017357 can be increased by dividing the daily dose into two portions (morning and evening), and beginning treatment with a low dose and titrating upward to a target of 250 mg twice daily.

Patients enrolled in this clinical study were randomized, double-blind, and placebo-controlled. There was a 7-day stabilization period for riluzole at a reduced dose of 50 mg QD. The patients were then randomized 3:1 to CK-2017357 or placebo for 14 days.

Figure 4:
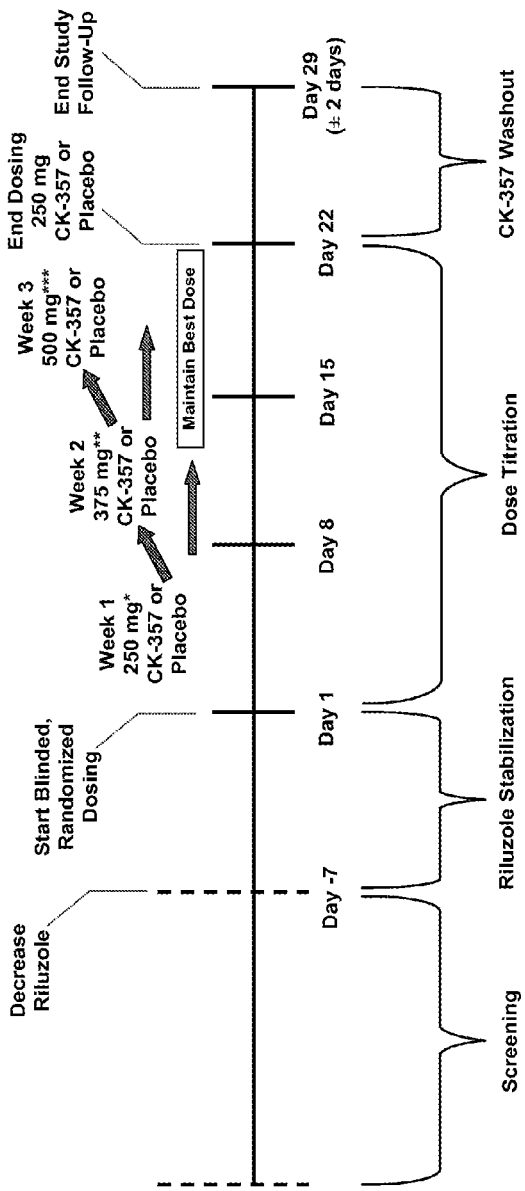
FIG. 4 shows a study flow diagram for a clinical study investigating a twice-daily dose titration regimen of CK-2017357 in patients with ALS.

The CK-2017357 titration regimen was as follows: dosing initiated at 125 mg twice daily for 7 days (250 mg total daily dose); on Day 8, up titration to 125 mg in the morning and 250 mg in the evening (375 mg total daily dose); on Day 15, up titration to 250 mg twice daily (500 mg total daily dose) continued through the morning dose on Day 22. Patients who did not tolerate a dose escalation returned to the previous tolerated dose level and remained at that dose level to complete the study. Placebo patients underwent a similar dummy dose titration to maintain the blind. FIG. 4 illustrates the study design.

Twenty-seven patients were treated in this study. All six patients randomized to placebo completed three weeks of dosing. Of the 21 patients randomized to treatment with CK-2017357, 14 were escalated to the highest total daily dose of 500 mg and completed three weeks of dosing. The most commonly reported treatment-emergent adverse event was dizziness, which was mild in 10 of the 12 patients in whom it occurred and only moderate in the other two. Dizziness was self-limited in 6 of 12 patients in whom it occurred. Encouraging trends toward increases in the ALS-FRS-R score and MVV were observed on CK-2017357 relative to placebo. Thus, this study suggests that CK-2017357 administered in a twice-daily, dose titration regimen is safe and well tolerated.

While the present invention has been described with reference to the specific embodiments described herein, it should be understood by those skilled in the art that various changes may be made and equivalents may be substituted without departing from the true spirit and scope of the invention. In addition, modifications may be made to adapt a particular situation, material, composition of matter and/or process to the objective, spirit and scope of the present invention. All such modifications are intended to be within the scope of the claims appended hereto.

The invention claimed is:

1. A method for treating ALS in a subject, comprising administering to the subject a total daily dose of 50 mg of riluzole and a total daily dose of between 125 mg and 500 mg of 6-ethynyl-1-(pentan-3-yl)-1H-imidazo[4,5-b]pyrazin-2(3H)-one.

2. The method of claim 1, wherein the riluzole is administered once a day.

3. The method of claim 2, wherein the 6-ethynyl-1-(pentan-3-yl)-1H-imidazo[4,5-b]pyrazin-2(3H)-one is administered once a day.

4. The method of claim 2, wherein the 6-ethynyl-1-(pentan-3-yl)-1H-imidazo[4,5-b]pyrazin-2(3H)-one is administered twice a day.

5. The method of claim 1, wherein the riluzole is administered twice a day.

6. The method of claim 5, wherein the 6-ethynyl-1-(pentan-3-yl)-1H-imidazo[4,5-b]pyrazin-2(3H)-one is administered once a day.

7. The method of claim 5, wherein the 6-ethynyl-1-(pentan-3-yl)-1H-imidazo[4,5-b]pyrazin-2(3H)-one is administered twice a day.

8. The method of claim 1, wherein the total daily dose of 6-ethynyl-1-(pentan-3-yl)-1H-imidazo[4,5-b]pyrazin-2(3H)-one is selected from the group consisting of 125 mg, 250 mg, 375 mg, and 500 mg.

9. The method of claim 1, wherein the riluzole is administered orally.

10. The method of claim 1, wherein the 6-ethynyl-1-(pentan-3-yl)-1H-imidazo[4,5-b]pyrazin-2(3H)-one is administered orally.

11. The method of claim 1, wherein the riluzole and the 6-ethynyl-1-(pentan-3-yl)-1H-imidazo[4,5-b]pyrazin-2(3H)-one are administered in separate pharmaceutical compositions.

12. The method of claim 1, wherein the riluzole and the 6-ethynyl-1-(pentan-3-yl)-1H-imidazo[4,5-b]pyrazin-2(3H)-one are administered in a single pharmaceutical composition.

13. The method of claim 1, wherein the total daily dose of riluzole is sufficient to result in a plasma $AUC_{last}$ of riluzole of at least 30 hr*μg/mL.

14. The method of claim 1, wherein the total daily dose of 6-ethynyl-1-(pentan-3-yl)-1H-imidazo[4,5-b]pyrazin-2(3H)-one is 125 mg.

15. The method of claim 1, wherein the total daily dose of 6-ethynyl-1-(pentan-3-yl)-1H-imidazo[4,5-b]pyrazin-2(3H)-one is 250 mg.

16. The method of claim 1, wherein the total daily dose of 6-ethynyl-1-(pentan-3-yl)-1H-imidazo[4,5-b]pyrazin-2(3H)-one is 375 mg.

17. The method of claim 1, wherein the total daily dose of 6-ethynyl-1-(pentan-3-yl)-1H-imidazo[4,5-b]pyrazin-2(3H)-one is 500 mg.

* * * * *